United States Patent [19]

Homeier

[11] 4,256,670

[45] Mar. 17, 1981

[54] PRODUCTION OF AMINO SUBSTITUTED AROMATIC COMPOUNDS

[75] Inventor: Edwin H. Homeier, Maywood, Ill.

[73] Assignee: UOP Inc., Des Plaines, Ill.

[21] Appl. No.: 94,537

[22] Filed: Nov. 15, 1979

[51] Int. Cl.³ .............................................. C07C 85/11
[52] U.S. Cl. ................... 564/416; 260/689; 564/422
[58] Field of Search ........................................ 260/580

[56] References Cited

U.S. PATENT DOCUMENTS

| | | | |
|---|---|---|---|
| 3,729,512 | 4/1973 | L'Eplattenier et al. | 260/580 |
| 3,944,615 | 3/1976 | Iqbal | 260/580 |
| 4,169,853 | 10/1979 | Knifton | 260/575 |

*Primary Examiner*—John Doll
*Attorney, Agent, or Firm*—James R. Hoatson, Jr.; Raymond H. Nelson; William H. Page, II

[57] ABSTRACT

Amino substituted aromatic compounds may be prepared by treating the corresponding nitro substituted aromatic compound at an elevated temperature and pressure in the presence of a catalytic composition of matter comprising metal catalyst complexes selected from the group consisting of metal phthalocyanines and metal carbonyls in which the metal portion of the compound is a Group VIII metal. Reaction conditions which may be employed will include temperatures ranging from about 90° to about 300° C. and pressures ranging from about 5 to about 5000 atmospheres.

8 Claims, No Drawings

PRODUCTION OF AMINO SUBSTITUTED AROMATIC COMPOUNDS

This invention relates to a process for the production of amino substituted aromatic compounds. More specifically, the invention is concerned with a process for treating nitro substituted aromatic compounds at reaction conditions in the presence of certain catalytic compositions of matter hereinafter set forth in greater detail.

Amino substituted aromatic compounds will find a wide variety of uses in the chemical field. For example, the most common of these compounds comprises aniline which is a well-known chemical. Aniline is useful in the preparation of rubber accelerators and antioxidants; in the manufacture of dyes and intermediates; in veterinary pharmaceuticals; in drugs; photographic chemicals; explosives; rocket fuel and petroleum refining. Likewise, the isomeric toluidines, which are also known as isomeric amino toluenes are useful in the manufacture of organic chemicals, in dyes, saccharin, printing textiles, vulcanization accelerators, as a test reagent for lignin, nitrite or phloroglucinol. Another amino substituted aromatic compound comprises xylidine which is usually present in a mixture of isomeric forms. These compounds are useful as dye intermediates; in organic syntheses and as an intermediate in the preparation of pharmaceuticals.

It is therefore an object of this invention to provide a process for the production of amino substituted aromatic compounds.

A further object of this invention is to provide a novel process for the production of amino substituted aromatic compounds utilizing metal catalyst complexes to effect the reaction.

In one aspect an embodiment of this invention resides in a process for the production of an amino substituted aromatic compound which comprises treating a nitro substituted aromatic compound at reaction conditions in the presence of a catalytic composition of matter comprising a metal catalyst complex selected from the group consisting of metal phthalocyanines and metal carbonyls, and recovering the resultant amino substituted aromatic compound.

A specific embodiment of this invention is found in a process for the production of an amino substituted aromatic compound which comprises treating nitrobenzene at a temperature in the range of from about 90° to about 300° C. and a pressure in the range of from about 5 to about 500 atmospheres in the presence of a catalyst comprising chlororhodium phthalocyanine tetrasulfonate, and recovering the resultant aniline.

Other objects and embodiments will be found in the following further detailed description of the present invention.

As hereinbefore set forth the present invention is concerned with a process for the production of amino substituted aromatic compounds. The process is effected by treating a nitro substituted aromatic compound at reaction conditions in the presence of certain metal catalyst complexes. The reaction conditions which may be employed to effect the reduction of the nitro substituted aromatic compound to the corresponding amino substituted aromatic compound will include elevated temperatures in the range of from about 90° to about 300° C. or more and pressures which may range from about 5 to about 5000 atmospheres. The superatmospheric pressures which are employed will be afforded by the introduction of a substantially inert gas such as nitrogen, carbon monoxide, helium, argon, etc., into the pressure resistant vessel which is utilized to effect said reaction.

Examples of metal catalyst complexes which may be employed to effect the synthesis of the amino substituted aromatic compound will include metal phthalocyanines and metal carbonyls in which the metal portion of the complex is a Group VIII metal. Specific examples of these compounds will include metal phthalocyanines such as platinum phthalocyanine, platinum phthalocyanine monosulfonate, platinum phthalocyanine disulfonate, platinum phthalocyanine tetrasulfonate, cobalt phthalocyanine, cobalt phthalocyanine monosulfonate, cobalt phthalocyanine disulfonate, cobalt phthalocyanine tetrasulfonate, ruthenium phthalocyanine, ruthenium phthalocyanine monosulfonate, ruthenium phthalocyanine disulfonate, ruthenium phthalocyanine tetrasulfonate, palladium phthalocyanine, palladium phthalocyanine monosulfonate, palladium phthalocyanine disulfonate, palladium phthalacyanine tetrasulfonate, chlororhodium phthalocyanine, chlororhodium phthalocyanine monosulfonate, chlororhodium phthalocyanine disulfonate, chlororhodium phthalocyanine tetrasulfonate, etc., metal carbonyls such as hexarhodiumhexadecylcarbonyl, tetrarhodiumdodecylcarbonyl, chlororhodiumcarbonyl dimer, hydridorhodiumtris(trimethylphosphene)carbonyl, hydridorhodiumtris(tri-n-butylphosphene)carbonyl, hydridorhodiumtris(triphenylphosphene)carbonyl, hydridorhodiumtris(trimethylphosphite)carbonyl, hydridorhodiumtris(triethylphosphite)carbonyl, hydridorhodiumtris(triphenylphosphite)carbonyl, tetrairidiumdodecylcarbonyl, bis(trimethylphosphino)iridiumcarbonyl chloride, bis(triethylphosphino)iridiumcarbonyl chloride, bis(tri-n-butylphosphino)-iridiumcarbonyl chloride, bis(triphenylphosphino)iridiumcarbonyl chloride, triruthenium dodecylcarbonyl, triosmiumdodecylcarbonyl, etc.

It is also contemplated within the scope of this invention that other metal compounds such as trisethylenediaminerhodium(III) chloride, cobalt carbonate, osmium trichloride, rhodium trichloride, iridium oxide, hexaammoniaruthenium(II) chloride, etc., may also be used as precursors which form the metal carbonyl complexes, although not necessarily with equivalent results. It is to be understood that the aforementioned compounds are only representative of the type of metal catalyst complexes which may be employed as catalysts, and that the present invention is not necessarily limited thereto.

Examples of nitro substituted aromatic compounds which may be employed as starting materials in the process of this invention will include nitrobenzene, o-nitrotoluene, m-nitrotoluene, p-nitrotoluene, 1-nitro-2,3-dimethylbenzene, 1-nitro-2,4-dimethylbenzene, 1-nitro-2,5-dimethylbenzene, 1-nitro-2,6-dimethylbenzene, 1-nitronaphthalene, 2-nitro-naphthalene, etc.

The process of the present invention may be effected in any suitable manner and may comprise either a batch or continuous type operation. For example, when a batch type of operation is employed, a quantity of the nitro substituted aromatic compound along with the catalyst comprising a metal complex of the type hereinbefore set forth in greater detail, is placed in a pressure resistant vessel such as an autoclave of the rotating, mixing or stirring type. The autoclave is then sealed and pressured to the desired level by the introduction of an inert gas such as carbon monoxide. Thereafter the autoclave is heated to the desired operating temperature and maintained thereat for a predetermined period of time which may range from about 0.5 up to about 10 hours or more in duration, said operating time being dependent upon the particular operating parameters of temperature and pressure which are used. At the end of the residence time, heating is discontinued and the autoclave is allowed to return to room temperature. After reaching room temperature the excess pressure is discharged and the autoclave is opened. The reaction mixture is recovered, separated from the catalyst by conventional means such as distillation, decantation, filtration, etc., and subjected to similar conventional means of recovery whereby the amino substituted aromatic compound is separated from any unreacted starting materials and/or unwanted side reactions which may have occurred during the residency period and recovered.

It is also contemplated within the scope of this invention that the process of the production of amino substituted aromatic compounds may be accomplished in a continuous manner of operation. When such a type of operation is to be employed, a reaction vessel containing the desired metal catalyst complex is maintained at the proper operating conditions of temperature and pressure while the nitro substituted aromatic compound is continuously charged to the reaction zone. After passage through the zone for a predetermined period of time, the reactor effluent is continuously withdrawn and subjected to conventional means of separation whereby the desired amino substituted aromatic compound is recovered while any unreacted starting material may be recycled to the reaction zone to form a portion of the feed stock.

Examples of amino substituted aromatic compounds which may be prepared according to the process of the invention will include aniline, o-toluidine, m-toluidine, p-toluidine, o-xylidine, m-xylidine, p-xylidine, 2,6-dimethylaniline, 1-aminonaphthalene, 2-aminonaphthalene, etc.

The following examples are given to illustrate the process of this invention. However, it is to be understood that these examples are given merely for purposes of illustration and that the present invention is not necessarily limited thereto.

EXAMPLE I

In this example, 23 grams of an aqueous solution of chlororhodium phthalocyanine tetrasulfonate (0.129 wt. % rhodium) along with 27 grams of nitrobenzene were placed in the glass liner of a rotating autoclave. Carbon monoxide was charged to the reactor until an initial operating pressure of 300 atmospheres was reached. The autoclave was then heated to a temperature of 190° C. and maintained in a range of from 190° to 193° C. for a period of 6 hours. During this residence time the maximum pressure of 494 atmospheres dropped to 465 atmospheres. At the end of the aforementioned period of time, heating was discontinued and the autoclave was allowed to return to room temperature, the final pressure at room temperature being 236 atmospheres. The excess pressure was discharged, the autoclave was opened and the reaction product comprising 12 grams of liquid was recovered therefrom. The analysis of the product by gas chromatography revealed that there was only one principal component present in the product mixture. Further analysis of the product by means of preparative gas liquid chromatography coupled with infrared analysis identified the principal component as aniline.

EXAMPLE II

In a manner similar to that set forth in Example I above 25 grams of p-nitrotoluene along with 25 grams of chlororhodiumdicarbonyl dimer may be placed in the glass liner of a rotating autoclave which may thereafter be sealed. Following the sealing of the autoclave carbon monoxide may be charged to the reactor until an initial operating pressure of 300 atmospheres is reached. The autoclave may then be heated to a temperature of 200° C. and maintained thereat for a period of 6 hours. At the end of the 6 hour period heating may be discontinued and after the autoclave has reached room temperature the excess pressure may be discharged. The autoclave may then be opened, the reaction product recovered therefrom, and subjected to various means of analysis such as gas chromatography, preparative gas liquid chromatography, infrared analysis, etc., to determine the presence of p-toluidine.

Similar results may be obtained when using a catalyst comprising ruthenium phthalocyanine in place of the chlororhodiumdicarbonyl dimer.

EXAMPLE III

To further illustrate the process of this invention 1-nitro-2,5-dimethylbenzene may be treated in a similar manner using rhodium carbonyl as the catalyst for the reaction. After treatment which may be effected at an elevated temperature of 190° C. and an initial operating pressure of 300 atmospheres of carbon monoxide for a period of 6 hours, the reaction product may be recovered and subjected to analysis of the type hereinbefore set forth in order to determine the presence of 2,5-xylidine.

I claim as my invention:

1. A process for the production of an amino substituted aromatic compound which comprises treating a nitro substituted aromatic compound at reaction conditions in the presence of a catalytic composition of matter consisting essentially of a metal phthalocyanine, and recovering the resultant amino substituted aromatic compound.

2. The process as set forth in claim 1 in which said reaction conditions include a temperature in the range of from about 90° to about 300° C. and a pressure in the range of from about 5 to about 5000 atmospheres.

3. The process as set forth in claim 2 in which said pressure is afforded by carbon monoxide.

4. The process as set forth in claim 1 in which said metal phthalocyanine catalytic composition of matter consist essentially of chlororhodium phthalocyanine tetrasulfonate.

5. The process as set forth in claim 1 in which said metal phthalocyanine catalytic composition of matter consist essentially of ruthenium phthalocyanine.

6. The process as set forth in claim 1 in which said nitro substituted aromatic compound is nitrobenzene and said amino substituted aromatic compound is aniline.

7. The process as set forth in claim 1 in which said nitro substituted aromatic compound is 1-nitro-2,5-dimethylbenzene and said amino substituted aromatic compound is 2,5-xylidine.

8. The process as set forth in claim 1 in which said nitro substituted aromatic compound is p-nitrotoluene and said amino substituted aromatic compound is p-toluidine.

* * * * *